United States Patent [19]

Minami et al.

[11] Patent Number: 5,037,969

[45] Date of Patent: Aug. 6, 1991

[54] GLYCOSYL DERIVATIVES AND USE THEREOF

[75] Inventors: Isao Minami, Osaka; Hayao Ueno, Suita; Masahiko Fujino, Takarazuka, all of Japan

[73] Assignee: Takeda Chemical Industries, Ltd., Osaka, Japan

[21] Appl. No.: 532,179

[22] Filed: Jun. 4, 1990

Related U.S. Application Data

[63] Continuation of Ser. No. 68,915, Jul. 2, 1987, abandoned.

[51] Int. Cl.$^5$ .............................................. C07H 15/08
[52] U.S. Cl. ...................................... 536/4.1; 536/1.1; 536/18.3; 536/120; 530/412
[58] Field of Search .................. 536/1.1, 4.1, 18.3, 536/120; 530/412

[56] References Cited

U.S. PATENT DOCUMENTS

| | | | |
|---|---|---|---|
| 3,222,357 | 12/1965 | Wismer et al. | 536/120 |
| 3,737,426 | 6/1973 | Throckmorton et al. | 536/18.3 |
| 4,002,531 | 1/1977 | Royer | 195/68 |
| 4,179,337 | 12/1979 | Davis et al. | 435/181 |
| 4,195,177 | 3/1980 | Inoue et al. | 536/120 |
| 4,261,973 | 4/1981 | Lee et al. | 424/78 |
| 4,329,338 | 5/1982 | Szego et al. | 514/27 |
| 4,330,677 | 5/1982 | Linke et al. | 514/824 |
| 4,528,106 | 7/1985 | Grolitzer | 536/4.1 |
| 4,585,858 | 4/1986 | Molotsky | 536/4.1 |
| 4,703,114 | 10/1987 | Mori et al. | 536/4.1 |
| 4,716,219 | 12/1987 | Eggimann et al. | 536/123 |

FOREIGN PATENT DOCUMENTS

| | | | |
|---|---|---|---|
| 0272247 | 3/1966 | Australia | 536/4.1 |
| 0721791 | 11/1965 | Canada | 536/4.1 |
| 0098110 | 11/1984 | European Pat. Off. | |
| 0154316 | 11/1985 | European Pat. Off. | |
| 2041636 | 2/1972 | Fed. Rep. of Germany | 536/120 |
| 1469472 | 4/1977 | United Kingdom | |

OTHER PUBLICATIONS

Frechet et al.; J. Am. Chem. Soc. 93(2):492–496 (1971).
Pitha et al.; Eur. J. Biochem. 94:11–18 (1979).
Bamford et al., Polymer Journal 19(5):475–483 (1987).
Abuchowski et al. Journal of Biological Chemistry, 252, 3578 (1977).
Takahashi et al., Biochemical and Biophysical Research Communications, 121, 261 (1984).
Veronese et al., Journal of Pharmacy and Pharmacology, 35, 757 (1983).
Nurddin et al., Biochem. J. 147, 71 (1975).
Slotboom et al., Biochemistry, 14, 5394 (1975).

Primary Examiner—Ronald W. Griffin
Assistant Examiner—Nancy S. Carson
Attorney, Agent, or Firm—David G. Conlin; Ronald I. Eisenstein

[57] ABSTRACT

The invention provides a compound of the formula (I): R—O—CH$_2$CH$_2$O$_m$CH$_2$)$_n$—Z wherein R is a glycosyl group, m is an optional positive integer, n is an integer from 1 to 3 and Z is —CHO, —CH$_2$OH or —COOH.

The compound of the formula (I'): R—O—CH$_2$CH$_2$O$_m$CH$_2$)$_n$—CHO wherein R, m and n are as defined above and the formula (I'''): R—OCH$_2$CH$_2$O$_m$CH$_2$)$_n$—COOH wherein R, m and n are as defined above is useful as a chemically modifying agent for protein.

The compound of the formula (I''): R—O—CH$_2$CH$_2$O$_m$CH$_2$)$_n$—CH$_2$OH wherein R, m and n are as defined above is useful as a protein fractionating agent.

4 Claims, 2 Drawing Sheets

GLYCOSYL DERIVATIVES AND USE THEREOF

This is a continuation of copending application Ser. No. 068,915, filed July 2, 1987, now abandoned.

BACKGROUND OF THE INVENTION

1. FIELD OF THE INVENTION

This invention relates to macromolecular compounds useful, for example, for introducing chemical modifier groups into biologically active proteins and for fractionating proteins.

2. DESCRIPTION OF THE PRIOR ART

Biologically active proteins are expected to be useful as drugs. With the recent progress in gene recombination technology, it has become possible to produce biologically active proteins in large quantities. However, when a biologically active protein is administered to a living body, its effective biological activity is sometimes not attained because of the rapid elimination thereof from the living body or because of unsatisfactory delivery thereof to the target cells or tissues. Furthermore, administration to humans of biologically active proteins obtained from organisms other than human, such as other animals or microorganisms, may induce severe symptoms due to immune responses. Therefore, in using these proteins as drugs, technical developments are desired which will delay the rate of clearance of proteins, which will deliver proteins to specific cells or tissues, or which will reduce their immunogenicity (antigenicity), while maintaining their biological activities.

For the above reasons, various techniques for chemical modifications of proteins have been attempted.

In addition, attempts have also been made to discover macromolecular compounds usable in the separation and purification of proteins.

SUMMARY OF THE INVENTION

While attempts have been made to modify biologically active proteins chemically as mentioned above, an object of the present invention is to provide macromolecular compounds that are useful for chemical modification of biologically active proteins.

Another object of the present invention is to provide macromolecular compounds usable in the fractionation of proteins.

The present inventors directed their attention to the biological properties of sugar chains of glycoproteins in living bodies. It is believed that the sugar chains play a very important role in the physicochemical properties of glycoproteins, in stabilization against proteases, in recognition mechanisms in organisms, or in protective action against recognition.

On the other hand, modification of proteins with polyethylene glycol derivatives leads to delayed clearance rate and reduced toxicity and/or antigenicity. Therefore, the inventors synthesized polyethylene glycol derivatives having a sugar chain moiety to modify proteins, and found that the proteins thus obtained showed the biological activity derived from the sugar chain moiety in addition to the characteristics of the polyethylene glycol-modified proteins, and exhibited increased circulatory half-life and reduced toxicity and antigenicity. It was also found that some of the derivatives can be used in protein fractionation, for instance.

The present inventors made further investigations on the basis of these findings and have now completed the present invention.

The present invention provides a compound of the formula $$R-O-CH_2CH_2O_mCH_2)_n-Z \qquad (I)$$

wherein R is a glycosyl group, m is an optional positive, integer, n is an integer from 1 to 3 and Z is —CHO, —CH$_2$OH or —COOH.

In the above formula (I), the glycosyl group represented by R may be of monosaccharide or oligosaccharide origin. The monosaccharide glycosyl group includes aldopentose-derived groups such as arabinopyranosyl, xylopyranosyl, lyxopyranosyl and ribofuranosyl, aldohexose-derived groups such as glucopyranosyl, galactopyranosyl, mannopyranosyl and fucopyranosyl, hexosamine-derived groups such as 2-amino-2-deoxyglucopyranosly, 2-amino-2-deoxygalactopyranosyl, 2-acetamido-2-deoxyglucopyranosyl and 2-acetamido-2-deoxygalactopyranosyl, and sialic acid-derived groups such as N-acetylneuraminyl, etc. The oligosaccharide glycosyl group includes, among others, disaccharide groups such as lactosyl, xylobiosyl, maltosyl, cellobiosyl, chitobiosyl, vicianosyl sambubiosyl, melibiosyl, epicellobiosyl, turanosyl, sucrosyl, lactulosyl and rutinosyl, trisaccharide groups such as raffinosyl, umbelliferosyl, sialyllactorsyl, and 6′-galactolactosyl, and tetrasaccharide groups such as difucosyllactosyl, lacto-N-tetraosyl and lacto-N-neotetraosyl.

When the glycosyl group is in the form of a uronic acid or a uronic acid derivative, it may be in a form having a free carboxyl group or in a form having an alkyl-esterified carboxyl group. Examples of such group are glucuronic acid-, galacturonic acid-, methyl glucuronate- and cellobiuronic acid-derived groups, etc.

The glycoside bond between the respective sugar units may be in α- or β-form.

When Z in the above formula (I) is —COOH, it may be in an active form. Said active form includes amides, active esters, active thioesters, etc.

Said amides include, for example, compounds derived from pyrazole, imidazole, 4-substituted imidazole, dimethylpyrazole, benzotriazole, etc. with the acyl group being bound to the nitrogen atom in the ring structure.

Said active esters include, for example, esters such as 4-nitrophenyl ester, 2,4-dinitrophenyl ester, trichlorophenyl ester, pentachlorophenyl ester and mesylphenyl ester and, in addition, esters with 1-hydroxy-1H-2-pyridone, N-hydroxysuccinimide, N-hydroxyphthalimide, benzotriazole, etc.

Said active thioesters include, for example, thioesters with heterocycle-thiols such as 2-pyridylthiol and 2-benzothiazolythiol.

In the above formula (I), the optional positive integer m is preferably about 200 or less, more preferably about 5 to 100.

The above compounds (I) can be produced, for example, according to the following reaction schemes:

(i) Production of compounds (I′) in which Z=CHO in formula (I):

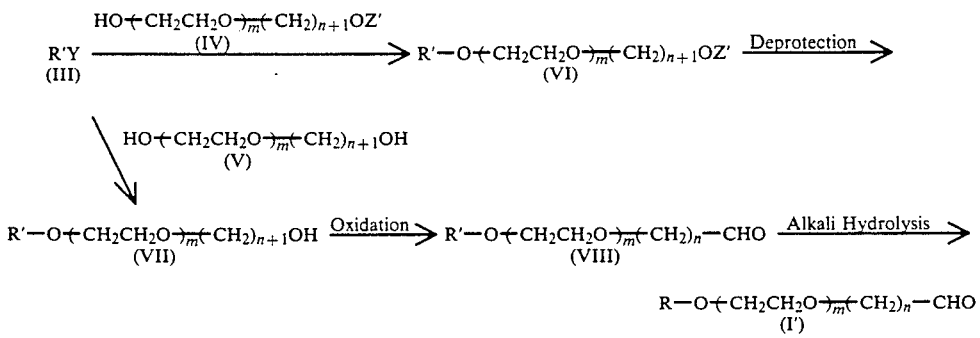

[In the above scheme, R, m and n are as defined above. R' is a monosaccharide or oligosaccharide group derived from R by protection of the hydroxyl and amino groups of R with an acyl group such as acetyl, Y is a halogen atom (e.g. fluorine atom, chlorine atom, bromine atom) or an acetate group, and Z' is a protective group such as 2-tetrahydropyranyl and benzyl.]

The compound (VI) can be synthesized from the compound(III) and the compound (IV) by using various glycosylation methods. Thus, for instance, when Y is a fluorine atom, it can be synthesized in the presence of a glycosylation catalyst such as $SnCl_2$—$AgClO_4$; when Y is a chlorine or bromine atom, by the König-Knorr method [Berichte, 34,957 (1901)] or by the ortho ester method [Recent Developments in the Chemistry of Natural Products, 4, 77 (1972)]; and when Y is an acetate group and R' is a hexosamine derivative having an acetamido group in the 2-position thereof, by the oxazoline method [Carbohydr. Research, 72, C12-L14 (1979)].

The reaction for converting compound (VI) to compound (VII) is preferably carried out in about 50–80% acetic acid-water at about 60°–100° C. for about 0.5-3 hours when Z' is 2-tetrahydropyranyl. When Z' is benzyl, the reaction is preferably carried out in a methanol, ethanol or acetic acid solution in the manner of catalytic hydrogenolysis using about 10% Pd-on-carbon.

The compound (VII) can also be obtained from compounds (III) and (V) by the same reaction as used in obtaining compound (VI) from compounds (III) and (IV).

The oxidation of compound (VII) to compound (VIII) is preferably carried out in dichloromethane at about −78° to −40° C. using oxalyl chloride, dimethyl sulfoxide and trietylamine.

The compound (I') can be prepared by subjecting compound (VIII) to alkali hydrolysis, preferably by reaction in an methanolic solution of sodium hydroxide at about 0°–4° C. for about 5–20 hours.

(ii) Production of compounds (I") in which $Z=CH_2OH$ in formula (I):

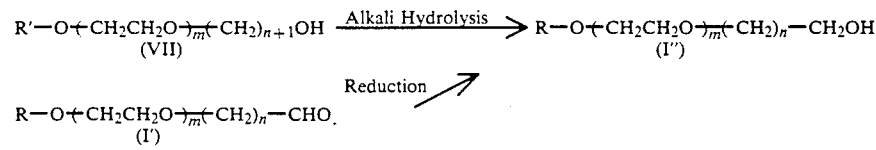

[In the above scheme, R,R', m and n are as defined above.]

The compound (I") can be prepared by subjecting the above-mentioned compound (VII) to alkali hydrolysis, preferably by reaction in a methanolic solution of sodium hydroxide at about 0°–4° C. for about 5–20 hours. The compound (I") can also be prepared by reacting the above-mentioned compound (I') with a reducing agent, such as sodium borohydride or sodium cyanoborchydride, in an aqueous solution.

(iii) Production of compounds (I''') in which $Z=$—COOH in formula (I):

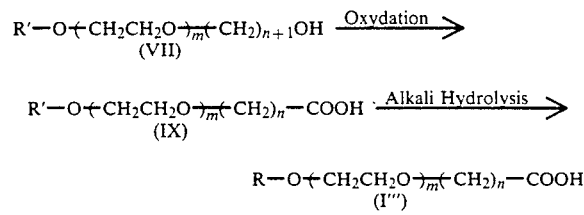

[In the above scheme, R, R', m and n are as defined above ]

The oxidation of the above-mentioned compound (VII) to compound (IX) can be carried out by the ruthenium tetroxide method [J. Org. Chem., 46, 3936–3938 (1981)].

The conversion of compound (IX) to compound(I''') can be effected by subjecting to alkali hydrolysis, preferably by treatment with a methanolic solution of sodium hydroxide at about 0°–4° C. for about 5–20 hours.

The reaction product after each of the above reactions can be purified by ordinary chemical methods such as extraction, concentration, recrystrallization, reprecipitation and chromatography.

When the compound to be used in each reaction has a group or groups which might possibly interfere with the reaction, said group or groups may be protected with a per se known protective group or groups (e.g. benzyl, trityl, benzyloxycarbonyl, tert-butyldimethylsilyl, benzylidene, isopropylidene). After reaction, the desired compound can be obtained by subjecting the reaction product to deprotection, which can be effected by a per se known method.

The compounds (I') and (I''') obtained by the present invention are useful for introducing chemical modifier groups into biologically active proteins.

The above-mentioned biologically active proteins may be ones derived from various animals including human, ones derived from microorganisms, ones derived from plants, genetically engineered ones, or synthetic ones. Thus, for example, there may be mentioned cytokines [e.g. interferons [interferon-α (IFN-α), interferon-β (IFN-β), interferon-γ (IFN-γ)], interleukin 2 (IL-2)], hormones [e.g. growth hormone, insulin], enzymes [e.g. urokinase, superoxide dismutase (SOD), asparaginase], and other proteins such as immunoglobulins, trypsin inhibitors, various proteases or peptidases, various cytochromes, islets activating proteins (IAP), various inhibitor proteins, and neocarzinostatin. Among them, recombinant IFNs (rIFN-α, rIFN-β, rIFN-γ) and rIl-2 produced by gene recombination techniques and SODs derived from animals and microorganisms are preferred biologically active proteins.

Said proteins preferably have a molecular weight of about 5,000 to about 50,000, more preferably about 10,000 to about 30,000.

The above-mentioned chemical modifier groups are bound to at least one of the primary amino groups of the biologically active proteins. The primary amino groups of proteins include N-terminal amino group and ε-amino groups of lysine resides.

The above-mentioned chemically-modified proteins can be produced, for example, by reacting a biologically active protein with an aldehyde of the formula

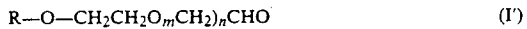

$$R\text{—}O\text{—}CH_2CH_2O_mCH_2)_nCHO \qquad (I')$$

wherein R, m and n are as defined above, in the presence of a reducing agent.

The reducing agent to be used in the above reaction is, for example, sodium borohydride, sodium cyanoborohydride, etc.

From the viewpoint of selectivity of reaction, sodium cyanoborohydride is preferred.

In carrying out the modification reaction, the compound (I') can be used in the amounts of about 1–10,000 mole equivalents and the boronic reducing agent in the amounts of about 1–50 mole equivalents to the biololgically active protein. The extent of modification can be arbitrarily selected by changing either the molar ratio of the protein to compound (I') or the concentrations of the protein and compound (I') in the reaction mixture. Any solvent which will not interfere with the reaction can be used as the reaction solvent. Examples are buffers such as phosphate buffer, Tris buffer and acetate buffer.

Organic solvents which do not inactivate the proteins or do not interfere with the reaction, such as lower alkanols (e.g. methanol, ethanol, i-propanol), tetrahydrofuran, dioxane, acetonitrile, dimethyl sulfoxide and dimethylformamide can be added. The reaction can be carried out under a wide pH range of about 3–12, but a pH around neutrality is preferable. The reaction temperature may be selected within the range in which the proteins are not denatured, preferably within the range of about 0° to 40° C. but this will vary depending upon the protein used. A reaction time of about 0.5–72 hours, generally about 3–30 hours, will be sufficient. The desired, chemically-modified proteins can be obtained by purifying the reaction mixture by conventional methods for protein purification, such as dialysis, salting out, ultrafiltration, ion exchange chromatography, gel filtration, high Performance liquid chromatography and electrophoresis. The extent of modification of amino groups can be calculated, for example, by acidolysis followed by amino acid analysis.

The above-mentioned chemically-modified proteins can also be produced, for example, by reacting a biologically active protein with a compound of the formula

$$R\text{—}O\text{—}CH_2CH_2O_mCH_2)_nCOOH \qquad (I''')$$

wherein R, m and n are as defined above, in the presence of a condensing agent such as a water-soluble carbodiimide.

The condensing agent to be used in the above reaction is, for example, 1-ethyl-3-(3-dimethylaminopropyl)-carbodiimide hydrochloride, 1-cyclohexyl-3-(2-morpholinoethyl)carbodiimide meso-paratoluenesulfonate, or the like.

In carrying out the modification, the compound (I''') can be used in the amounts of about 1–10,000 mole equivalents and the water-soluble carbodiimide in the amounts of about 1–5 mole equivalents to the biologically active protein. The extent of modification can be selected arbitrarily by changing either the molar ratio of the protein to the compound (I''') or the concentrations of the protein and the compound (I''') in the reaction mixture. Any solvent which will not interfere with the reaction can be used. As such solvent, a buffer such as phosphate buffer, Tris buffer and acetate buffer are included. Organic solvents which do not inactivate the proteins or interfere the reaction, such as lower alkanols (e.g. methanol, ethanol, i-propanol),acetonitrile, tetrahydrofuran, dioxane, dimethyl suflfoxide and dimethylformamide can be added. The reaction can be carried out under a wide pH range of about 4–10 but a pH around neutrality is preferable. The reaction temperature may be selected within the range in which denaturation of the protein does not occur, but is preferably, within about 0° to 40° C. but this will vary depending upon the protein used. A reaction time of about 0.5–72 hours, generally about 3–30 hours, will be sufficient. The desired, chemically-modified proteins can be obtained by purifying the reaction mixture by a conventional methods for protein purification, such as dialysis, salting out ultrafiltration, ion exchange chromatography and filtration, high performance liquid chromatography and electrophoresis. The extent of modification of amino groups in the protein can be determined by the 2,4,6-trinitrobenzenexulfonic acid method [Analytical Biochemist - 14, 328–336 (1966)].

In using protein modification, (I''') can be converted to an active ester or active amide and then used in the same was as (I''') itself. In this case, the use of a condensing agent like water-soluble carbodiimides, etc. is not necessary.

The chemically-modified proteins thus obtained have at least one primary amino group modified with a group of the formula:

$$R\text{—}O\text{—}CH_2CH_2O_mCH_2)_nX\text{—} \qquad (II)$$

wherein X is —CH₂— or —CO— and R, m and n are as defined above.

When the protein to be chemically modified has amino groups only at its N-terminus, the chemically-modified protein obtained by the above manner has the group of formula (II) directly bound to said amino groups. When the biologically active protein has one or more lysine residues, part of the ε-amino groups, preferably about 5-80% (average), more preferably about 10-60% (average), are directly bound to the group of formula (II). In this case, the N-terminal amino group may have or may not have the group of formula (II) directly bound thereto.

The above chemically-modified proteins have useful biological activities similar to that of the corresponding unmodified biologically active proteins and are useful as drugs, etc.

Compared to the corresponding known unmodified biologically active proteins, the chemically-modified Proteins obtained by the present process are reduced in clearance, thus remaining effective for a longer period, improved in delivery to specific cells and tissues and reduced in toxicity and antigenicity. Accordingly, they can be used safely in the same manner and for the same purposes as known biologically active proteins.

The above chemically-modified proteins can be administered orally or parenterally to mammals (e.g. monkey, dog, swine, rabbit, mouse, human) in the form of suitable pharmaceutical compositions (e.g. capsules, injections) prepared by using conventional known carriers, diluents, etc.

For example, the above chemically-modified rIL-2 can be used as a preventive or therapeutic agent for tumors; it is administered in similar doses as unmodified rIL-2, namely in very low doses in the form of injections, capsules, etc.

The above chemically-modified rIFN-γ, when used as an antiviral, antitumor, cell growth inhibiting or immunopotentiating agent, is administered to human adults at a dose of about $1.0 \times 10^5$ to $1.0 \times 10^8$ unit/day, intravenously, intramuscularly or other route.

The above chemically-modified rIFN-αA, when used as an antitumor or antiviral agent, may be administered to patients in about $1.0 \times 10^5$ to $1.0 \times 10^6$ unit/day as amount of rIFN-αA.

In its use as an antiinflammatory agent, the above chemically-modified SOD can be administered to mammals, for example, in the form of tablets, injections, etc. in a daily dose of about 1-5 mg/kg on the SOD basis.

The compounds(I'') can be used in protein fractionation in the same manner as polyethylene glycol. The concentration used in this case is about 0-70%. Proteins are usually obtained as precipitates. However, proteins are sometimes obtained as highly concentrated solutions thereof since the formation of precipitates is much effected by the concentration of compound (I''), the salt concentration, the ion strength, pH, etc. For example, in fractionating human plasma proteins by using compound (I''), to a human plasma protein solution cooled to about 4° C., a 50% solution of the compound (I'') is added to prescribed concentration of (I'') with stirring. The mixture is allowed to stand for about 10 minutes and the resulting precipitate is separated by centrifugation at 35,000 g for 30 minutes. By stepwise increasing the concentration of the compound (I'') in the supernatant, the plasma proteins can be fractionated.

The compounds (I'') can also be used in aqueous two-phase partition methods by forming two-phase systems with other polymers, e.g. dextran, etc. A concentration of about 0-70%, usually about 1-30%, is used in this case. In a typical example for protein fractionation by an aqueous two-phase partition method, a 0.01 M buffer containing 4.4% of compound (I''), 7.0% of dextran T-500 (Pharmacia, Sweden) and 0.1 M NaCl is used. The mixture is stirred thoroughly and then allowed to stand at room temperature for at least 10 minutes. By subsequent centrifugation at 2,000 g for 5 minutes, two-phases are separated well. A fraction that contains the desired protein can be obtained by taking either the upper layer or the lower layer.

In each case, the use of the compounds(I'') can be expected to produce the bio-affinity effect due to the sugar chain in addition to partition effect derived from polyethylene glycol.

In the present specification, amino acids, in some cases, are represented by abbreviations based on the IUPAC-IUB nomenclature (Commision on Biochemical Nomenclature), Thus, Lys: Lysine

EXAMPLES OF THE PREFERRED EMBODIMENT

Figure 1A:
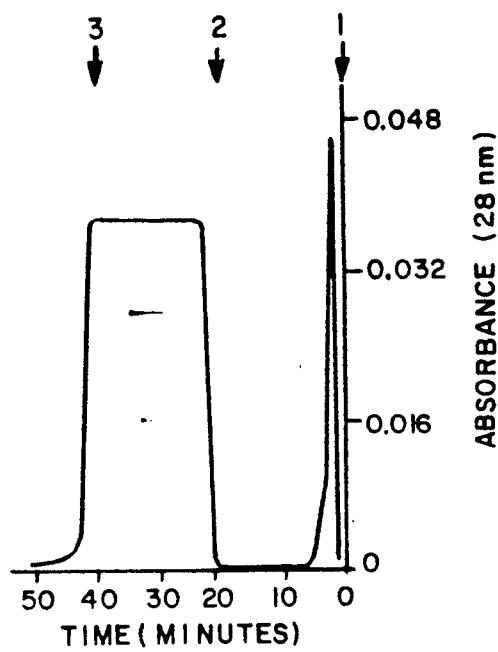
FIG. 1 and FIG. 2 show binding capability to the immobilized lectins of the modified proteins described in Reference Example 2 and Reference Example 3, respectively.

The following working examples and reference examples are further illustrative of the present invention but are by no means limitative of the present invention.

EXAMPLE 1

Synthesis of β-D-galactopyranosylpolyethylene glycol aldehyde (i) Synthesis of 2,3,4,6-tetra-O-acetyl-β-D-galactopyranosylpolyethylene glycol To a solution of 948 mg (0.79 m mol) of polyethylene glycol mono-2-tetrahydropyranyl ether (mean molecular weight: 1,200) in 8 ml of nitromethane, 1.4 g (5.54 m mol) of mercuric cyanide, 1 g of Drierite (W. A. Hammond Drierite Company) and 433 mg (3.73 m mol) of N,N,N',N'-tetramethylurea were added. The mixture was stirred at room temperature for 10 minutes. To this solution, 1.53 g (3.73 m mol) of acetobromogalactose in 8 ml of anhydrous benzene was added dropwise, and the mixture was stirred at 55° C. for 24 hours in the dark. After cooling, the reaction mixture was dissolved in chloroform and washed successively with cold water, a solution of 3.7 g of potassium iodide and 3 g of sodium hydrogen carbonate in 60 ml of water and cold water. After drying over anhydrous sodium sulfate, the solvent was evaporated under reduced pressure, and the crude product obtained was purified by column chromatography [silica gel: 40 g; eluent: chloroform-methanol (95:5)] to give 520 mg of the tetrahydropyranyl ether of 2,3,4,6-tetra-O-acetyl-β-D-galactopyranosylpolyethylene glycol. This was dissolved in 4.5 ml of acetic acid-water (2:1) and the solution was stirred at 70° C. for 1.5 hours. Toluene was added to the reaction mixture and the resultant mixture was evaporated to dryness under reduced pressure The crude product thus obtained was purified by column chromatography [silica gel: 10 g; eluent: chloroform-methanol (9:1)] to give 370 mg (33%) of the product (light yellow oil).

NMR (90 MHz, CDCl$_3$) β: 1.97, 2.05 and 2.14 (12H, each s), 3.67, 4.57 (1H, d), 5.05–5.42 (3H, m).

(ii) Synthesis of
2,3,4,6-tetra-O-acetyl-β-D-galactopyranosylpolyethylene glycol aldehyde To a solution of 46 μl (0.52 m mol) of oxalyl chloride in 0.74 ml of methylene chloride, 0.15 ml of a methylene chloride solution containing 74 μl (1.04 m mol) of dimethyl sulfoxide was added dropwise below −60° C.. Five minutes later, 0.6 ml of a methylene chloride solution containing 370 mg (0.26 m mol) of the alcohol obtained in step (i) was added dropwise. After 15 minutes, 0.34 ml of triethylamine was added dropwise, and the mixture was stirred for 5 minutes. After the temperature was allowed to rise to 0° C., water was added to the reaction mixture. The resultant mixture was extracted with methylene chloride, and the organic layer was dried over anhydrous sodium sulfate. The solvent was evaporated under reduced pressure, and the crude product was purified by column chromatography [silica gel: 10 g; eluent: chloroform-methanol (9:1)] to give 290 mg (78%) of the product (light yellow oil).

NMR (90 MHz, CDCl ) δ: 1.97, 2.04 and 2.13 (12H, each s), 3.66, 4.56 (1H, d), 5.03–5.40 (3H, m).

(iii) Synthesis of β-D-galactopyranosylpolyethylene glycol aldehyde

To a solution of 32 mg (0.8 m mol) of sodium hydroxide in 1.6 ml of methanol was added 290 mg (0.2 m mol) of the aldehyde obtained in step (ii). The mixture was allowed to stand in a refrigerator for 15 hours. The reaction mixture was neutralized by addition of acetic acid, and the solvent was evaporated under reduced pressure. The crude product obtained was purified by column chromatography [silica gel: 3 g; eluent: chloroform-methanol (9:1)] to give 110 mg (43%) of the product (colorless oil).

2,4-Dinitrophenylhydrazine reaction: positive;
Anthrone reaction: positive.

EXAMPLE 2

Synthesis of
2-acetamido-2-deoxy-β-D-glucopyranosylpolyethylene glycol aldehyde (i) Synthesis of
2-acetamido-3,4,6-tri-O-acetyl-2-deoxy-β-D-glucopyranosylpolyethylene glycol The mixture of 10 ml of methylene chloride, 340 mg (2.1 m mol) of ferric chloride, 244 mg (2.1 m mol) of N,N',N'-tetramethylurea and 545 mg of Drierite was stirred at room temperature for 10 minutes and 545 mg (1.4 m mol) of 2-acetamido-1,3,4,6-tetra-O-acetyl-2-deoxy-β-D-glucopyranose was added. After stirring for 1 hour, 672 mg (0.56 m mol) of polyethylene glycol mono-2-tetrahydropyranyl ether (mean molecular weight: 1,200) was added and the resultant mixture was further stirred at room temperature for 2 days. The reaction mixture was poured into 15 ml of saturated aqueous sodium hydrogen carbonate and extracted with chloroform, and the organic layer was dried over anhydrous sodium sulfate. The solvent was evaporated under reduced pressure, and the crude product obtained was purified by column chromatography [silica gel: 10 g; eluent: chloroform-methanol (95:5)] to give 0.8 g of the tetrahydropyranyl ether of 2-acetamido-3,4,6-tri-O-acetyl-2-deoxy-β-D-glucopyranosylpolyethylene glycol. This was dissolved in 6 ml of an acetic acid-water mixture (2:1) and the solution was stirred at 70° C. for 1.5 hours. Toluene was added to the reaction mixture and the resultant mixture was evaporated to dryness under reduced pressure The crude product thus obtained was purified by column chromatography [silica gel: 10 g; eluent: chloroform-methanol (9:1)] to give 0.5 g (67%) of the product (light yellow oil).

NMR (90 MHz, CDCl ) δ: 1.95, 1.99 and 2.07 (12H, each s), 3.65, 4.78 (1H, d), 5.02–5.13 (2H, m), 6.60 (1H, d).

(ii) Synthesis of
2-acetamido-3,4,6-tri-O-acetyl-2-deoxy-β-D-glucopyranosylpolyethylene glycol aldehyde The alcohol (1.1 g, 0.77 m mol) obtained in step (i) was treated in the same manner as described in Example 1-(ii) to give 818 mg (74%) of the product (light yellow oil).

NMR (90 MHz, CDCl ) δ: 1.95, 1.98 and 2.03 (12H, each s), 3.65 4.78 (1H, d), 5.02–5.13 (2H, m), 6.67 (1H, d).

(iii) Synthesis of
2-acetamido-2-deoxy-β-D-glucopyranosylpolyethylene glycol aldehyde The aldehyde (818 mg, 0.57 m mol) obtained in step (ii) was treated in the same manner as described in Example 1-(iii) to give 370 mg (50%) of the product (colorless oil).

NMR (90 MHz, CDCl$_3$) β: 2.04 (3H, s), 3.67, 4.63 (1H, d), 7.16 (1H, d).

2,4-Dinitrophenylhydrazine reaction: positive.

EXAMPLE 3

Synthesis of β-D-glucopyranosylpolyethylene glycol aldehyde (i) Synthesis of
2,3,4,6-tetra-O-acetyl-β-D-glucopyranosylpolyethylene glycol To a solution of 10.8 g (18 m mol) of polyethylene glycol (mean molecular weight: 600) in 18 ml of nitromethane, 2.27 g (9 m mol) of mercuric cyanide, 6 g of Drierite and 0.7 g (6 m mol) of N,N,N',N'-tetramethylurea were added, and the mixture was stirred at room temperature for 10 minutes. To this solution, 2.46 g (6 m mol) of acetobromoglucose in 18 ml of anhydrous benzene was added dropwise, and the resultant mixture was stirred at 55° C. for 24 hours in the dark. After cooling, the reaction mixture was dissolved in chloroform and washed successively with cold water, a solution of 6 g of potassium iodide and 4.8 g of sodium hydrogen carbonate in 96 ml of water, and cold water, and the organic layer was dried over anhydrous sodium sulfate. After removal of the solvent under reduced pressure, the crude product was purified by column chromatography [silica gel: 50 g; eluent: chloroform-methanol (97:3)] to give 1.7 g (30%) of the product (colorless oil).

NMR (90 MHz, CDCl$_3$) δ: 1.99, 2.02, 2.03 and 2.07 (12H, each s), 3.66, 4.61 (1H, d), 4.88–5.33 (3H, m).

(ii) Synthesis of
2,3,4,6-tetra-O-acetyl-β-D-glucopyranosylpolyethylene glycol aldehyde The alcohol (1.64 g, 1.76 m mol) obtained in step (i) was treated in the same manner as described in Example 1-(ii) to give 970 mg (60%) of the product (colorless oil).

NMR (90 MHz, CDCl$_3$) $\beta$: 1.99, 2.01, 2.03 and 2.07 (12H, each s), 3.66, 4.60 (1H, d), 4.66 and 9.76 (1H, CHO), 4.87–5.23 (3H, m).

(iii) Synthesis of $\beta$-D-glucopyranosylpolyethylene glycol aldehyde

The aldehyde (970 mg, 1.04 m mol) obtained in step (ii) was treated in the same manner as stated in Example 1-(iii) to give 340 mg (43%) of the product (colorless oil).

2,4-Dinitrophenylhydrazine reaction: positive; Anthrone reaction: positive.

EXAMPLE 4

Synthesis of $\beta$-D-galactopyranosylpolyethylene glycol monocarboxylic acid (i) Synthesis of 2,3,4,6-tetra-O-acetyl-$\beta$-D-galactopyranosylpolyethylene glycol monocarboxylic acid The mixture of 834 mg (0.9 m mol) of 2,3,4,6-tetra-O-acetyl-$\beta$-D-galactoPyranosylpolyethylene glycol synthesized from polyethylene glycol having a mean molecular weight of 600 and acetobromogalactose by following the procedure described in Example 3-(i), 1.8 ml of carbon tetrachloride, 1.8 ml of acetonitrile and 2.7 ml of water was stirred vigorously. Immediately after addition of 577 mg (2.3 m mol) of NaIO$_4$ to this biphasic solution, 7 mg (0.027 m mol) of crystalline ruthenium trichloride was added and the reaction was allowed to proceed at room temperature for 1 hour. Then the phases were separated and the upper aqueous phase was extracted 3 times with 10-ml portions of methylene chloride. The combined organic extracts were dried over anhydrous magnesium sulfate and evaporated to dryness under reduced pressure to give 810 g of a light yellow oil.

NMR (90 MHz, CDCl ) $\beta$: 1.98, 2.05 and 2.15 (12H, each s), 3.65, 4.56 (1H, d), 5.00–5.43 (3H, m).

(ii) Synthesis of $\beta$-D-galactopyranosylpolyethylene glycol monocarboxylic acid To a solution of 174 mg (4.4 m mol) of sodium hydroxide in 8.7 ml of methanol was added 810 mg (0.87 m mol) of the monocarboxylic acid obtained in step (i), and the reaction was allowed to proceed overnight in a refrigerator. The reaction mixture was neutralized by addition of acetic acid, and the solvent was evaporated under reduced pressure. The crude product obtained was purified by column chromatography [silica gel: 20 g; eluent: chloroform-methanol-acetic acid (7:3:1)]. After removal of the eluent under reduced pressure, the residue was dissolved in chloroform. The chloroform layer was washed with water and dried over anhydrous sodium sulfate. The solvent was evaporated under reduced pressure to give 30 mg of the product (light yellow oil).

NMR (90 MHz, CDCl ) $\beta$: 3.66 (—OCH$_2$CH$_2$O—).
IR: 1733 cm$^{-1}$ (COOH).
Anthrone reaction: positive.

EXAMPLE 5

Synthesis of $\beta$-D-galactopyranosylpolyethylene glycol 2,3,4,6-Tetra-O-acetyl-$\beta$-D-galactopyranosylpolyethylene glycol (494 mg, 0.53 m mol) synthesized from polyethylene glycol having a mean molecular weight of 600 and acetobromogalactose by following the procedure described in Example 3-(i) was treated in the same manner as cited in Example 1-(iii) to give 190 mg of the product (light yellow oil).

NMR (90 MHz, CDCl$_3$) $\beta$: 3.66 (—OCH$_2$CH$_2$O—).
Anthrone reaction: positive.

EXAMPLE 6

Synthesis of $\beta$-D-galactopyranosyldiethylene glycol aldehyde (i) Synthesis of 2,3,4,6-tetra-O-acetyl-$\beta$-D-glucopyranosyldiethylene glycol benzyl ether To a solution of 589 mg (3 m mol) of diethylene glycol monobenzyl ether in 19.5 ml of nitromethane, 3.41 g (13.5 m mol) of mercuric cyanide and 3 g of Drierite were added, and the mixture was stirred at room temperature for 10 minutes. To this solution, 3.69 mg (9 m mol) of acetobromogalactose in 19.5 ml of anhydrous benzene was added dropwise, and the mixture was stirred at 55° C. for 24 hours in the dark. After cooling, the reaction mixture was dissolved in chloroform and the organic layer was washed successively with cold water, a solution of 18 g of potassium iodide and 14.6 g of sodium hydrogen carbonate in 300 ml of water, and cold water. The organic layer was dried over anhydrous sodium sulfate. The solvent was then evaporated under reduced pressure, and the crude product obtained was purified by column chromatography [silica gel: 50 g; eluent: chloroform] to give 1.45 g (92%) of the product (colorless oil).

NMR (90 MHz, CDCl$_3$) $\beta$: 1.95, 2.00, 2.02 and 2.12 (12H, each s), 4.55 and 4.93 (1H, each d), 4.55 (2H, s), 5.02–5.45 (3H, m), 7.31 (5H, s).

(ii) Synthesis of 2,3,4,6-tetra-O-acetyl-$\beta$-D-galactopyranosyldiethylene glycol A solution of 1.37 g (2.6 m mol) of the benzyl ether obtained in step (i) in 32.5 ml of acetic acid was added to 0.96 g of 10% Pd-C (50% wet), and the mixture was stirred under a hydrogen atmosphere at room temperature for 5 hours. The catalyst was then filtered off and toluene was added to the filtrate. The solvent was evaporated to dryness under reduced pressure to give the crude product, which was purified by column chromatography [silica gel: 30 g; eluent: chloroform-methanol (97:3)] to give 0.8 g (71%) of the product (colorless oil).

NMR (90 MHz, CDCl$_3$) $\beta$: 1.97, 2.03, 2.05 and 2.13 (12H, each s), 4.55 and 4.94 (1H, d), 5.05–5.40 (3H, m).

(iii) Synthesis of 2,3,4,6-tetra-O-acetyl-$\beta$-D-galactopyranosyldiethylene glycol aldehyde The alcohol (0.8 g, 1.8 m mol) obtained in step (ii) was treated in the same manner as described in Example 1-(ii) to give 0.67 g (86%) of the product (colorless oil).

NMR (90 MHz, CDCl$_3$) $\beta$: 1.97, 2.03, 2.06 and 2.14 (12H, each s), 4.57 and 4.95 (1H, each d), 5.04–5.41 (3H, m), 9.71 (s).

(iv) Synthesis of $\beta$-D-galactopyranosyldiethylene glycol aldehyde

The aldehyde (660 mg, 1.52 m mol) obtained in step (iii) was treated in the same manner as described in Example 1-(iii) to give 185 mg (46%) of the product (colorless powder).

2,4-Dinitrophenylhydrazine reaction: positive; Anthrone reaction: positive.

REFERENCE EXAMPLE 1

Production of polyethylene glycol-modified IFN-αA (i) A solution of 0.68 ml (8.8 m mol) of dimethyl sulfoxide in 2 ml of methylene chloride was added dropwise to a solution of 0.4 ml (4.4 m mol) of oxalyl chloride in 10 ml of methylene chloride below −60° C.. After 5 minutes, a solution of 5 g (4 m mol) of polyethylene glycol mono-2-tetrahydropyranyl ether having a mean molecular weight of 1,200 in 4 ml of methylene chloride was added dropwise After 15 minutes, 2.8 ml of triethylamine was added, and the resultant mixture was stirred for 5 minutes. The temperature was allowed to rise to 0° C. and water was added. The mixture was extracted with methylene chloride, and the organic layer was dried over anhydrous sodium sulfate. After removal of the solvent under reduced pressure, 30 ml of an acetic acid-water mixture (2:1) was added to the residue, and the mixture was stirred at 70° C. for 1.5 hours. Toluene was added to the reaction mixture, and the resultant mixture was evaporated to dryness under reduced pressure. The crude product thus obtained was purified by column chromatography [silica gel: 40 g; eluent: chloroform-methanol (95:5)] to give 3.5 g (80%) of methoxypolyethylene glycol monoaldehyde (light yellow solid).

NMR (90 MHz, CDCl$_3$) $\beta$: 3.65, 4.15 and 9.72 (1H, s).

(ii) An IFN-α (rIFN-αA) solution was prepared by the method described in Japanese Unexamined Patent Publication No. 79897/1982 and 5 ml (5 mg as protein) of the solution was dialyzed against 0.2 M phosphate buffer (pH 7.0) containing 0.15 M sodium chloride at 4° C. overnight. The dialyzate was taken out and 45 mg of the polyethylene glycol monoaldehyde (mean molecular weight 1,100) obtained in Reference Example 1-(i) was added thereto. The mixture was stirred at 4° C. for 5 hours. Then, 14 mg of sodium cyanoborohydride was added and stirring was continued at 4° C. further for 24 hours. The reaction mixture was dialyzed against 25 mM ammonium acetate buffer (pH 5.0) containing 0.15 M sodium chloride at 4° C. for 24 hours. The dialyzate was separated by Sephadex G-75 column (2.2×45 cm). Elution was carried out with 25 mM ammonium acetate buffer (pH 5.0) containing 0.15 M sodium chloride, and 31 ml of a main protein fraction was collected. The protein content of this fraction determined by the Lowry method using bovine serum albumin as a standard was 76 μg/ml. Amino acid analysis of acid hydrolysate indicated that 4.5 of 11 Lys residues in IFN-α had been modified. The activity measured by enzyme immunoassay was $0.88 \times 10^7$ international units per milligram.

REFERENCE EXAMPLE 2

Production of β-D-galactopyranosyl-polyethylene glycol-modified IFN-αA (i) An IFN-α (rIFN-αA) solution was prepared by the method described in Japanese Unexamined Patent Publication No. 79897/1982 and 5 ml (5 mg as protein) of the solution was dialyzed against 0.2 M phosphate buffer (pH 7.0) containing 0.15 M sodium chloride at 4° C. overnight. The dialyzate was taken out and 84 mg of the aldehyde (mean molecular weight 1,300) obtained in Example 1-(iii) was added thereto. The mixture was stirred at 4° C. for 5 hours. Then, 21 mg of sodium cyanoborohydride was added and the mixture was further stirred at 4° C. for 24 hours. The reaction mixture was dialyzed against 25 mM ammonium acetate buffer (pH 5.0) containing 0.15 M sodium chloride at 4° C. for 24 hours. The dialyzate was taken out and applied to Sephadex G-75 column (2.2×45 cm) and eluted with 25 mM ammonium acetate buffer (pH 5.0) containing 0.15 M sodium chloride, and a main protein fraction (76 ml) was collected. The protein content of this fraction determined by the Lowry method using bovine serum albumin as a standard was 54 μg/ml. Amino acid analysis following acidolysis revealed that 2.4 of 11 Lys residues had been modified. The activity determined by enzyme immunoassay was $0.25 \times 10^8$ international units per milligram.

(ii) Unmodified IFN-α, the polyethylene glycol-modified IFN-α obtained in Reference Example 1-(ii) and the β-D-galactopyranosylpolyethylene glycol-modified IFN-α obtained in Reference Example 2-(i) were subjected to affinity chromatography using RCA120-Agarose (Hohnen Seiyu), an agarose gel coupled with wheat germ lectin, which is capable of recognizing and binding specifically to a nonreducing β-galactose end-group. Unmodified IFN-α and the polyethylene glycol-modified IFN-α were not adsorbed on the column but passed through it, while the β-D-galactopyranosylpolyethylene glycol-modified IFN-α was found to be adsorbed on RCA120-Agarose.

Figure 1B:
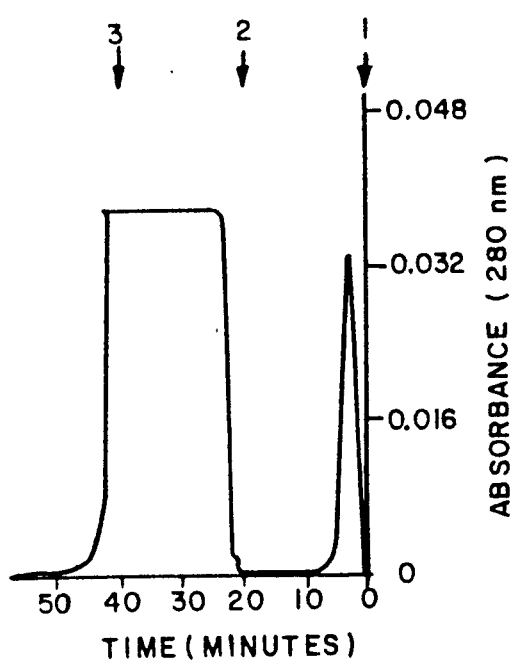
Figure 1C:
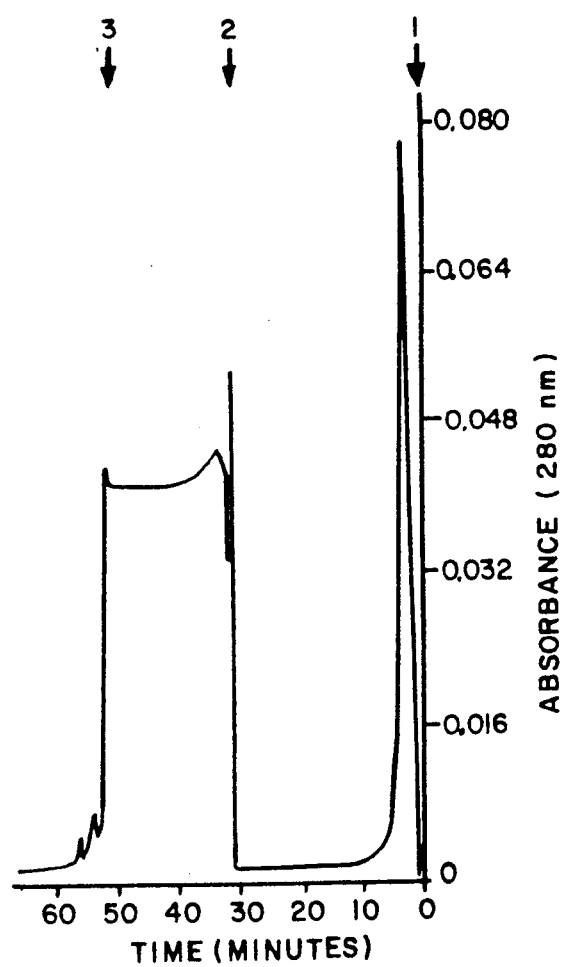
Figure 2A:
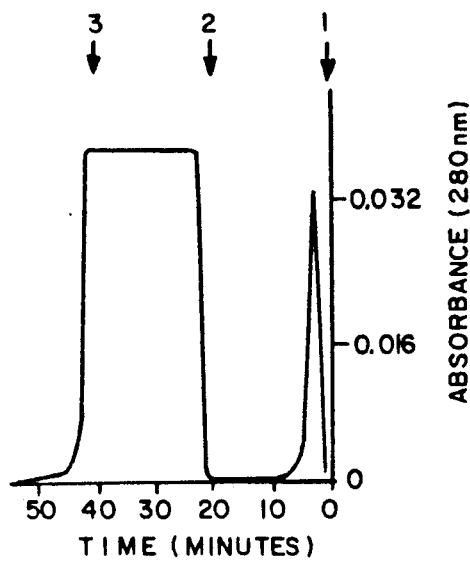
Figure 2B:
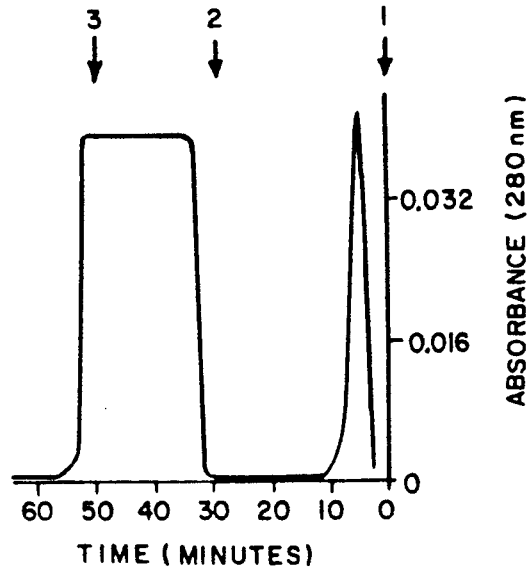
Figure 2C:
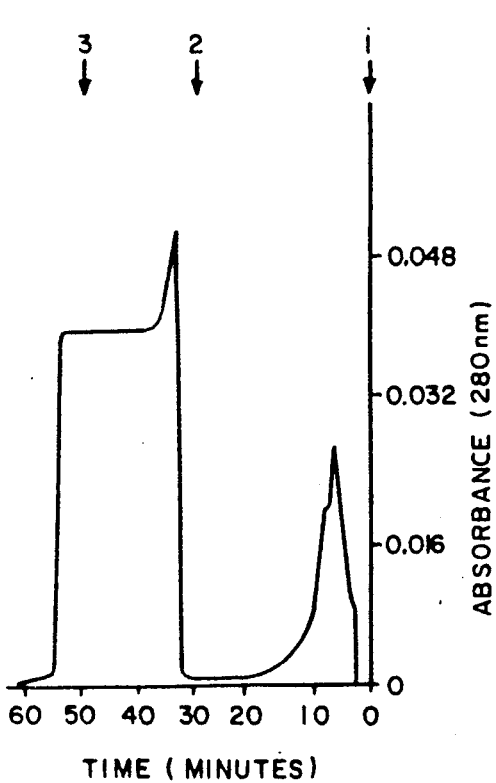
Figure 2D:
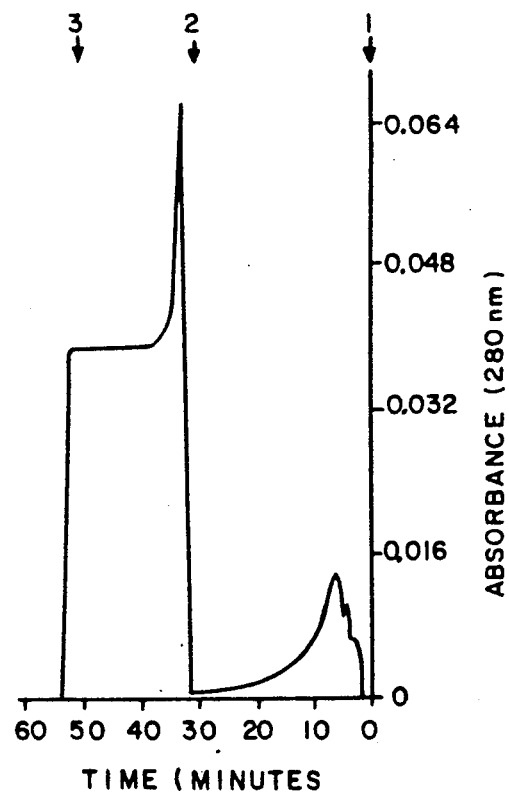

The results of affinity chromatography are shown in FIG. 1. In FIG. 1, charts (a), (b) and (c) show the elution patterns of unmodified IFN-α, the polyethylene glycol-modified IFN-α and the β-D-galactopyranosyl-polyethylene glycol-modified IFN-α, respectively, obtained by monitoring the absorbance at 280 nm. In each chart, arrow 1 indicates the time when each sample solution dissolved in 0.1 M phosphate buffer (pH 7.2) containing 0.15 M sodium chloride was charged, arrow 2 the time when the eluent was changed from 0.1 M phosphate buffer (pH 7.2) containing 0.15 M sodium chloride to 0.1 M phosphate buffer (pH 7.2) containing 10 mM β-D-galactopyranoside and 0.15 M sodium chloride, and arrow 3 the time when the eluent was changed to the initial 0.1 M phosphate buffer (pH 7.2) containing 0.15 M sodium chloride.

REFERENCE EXAMPLE 3

Production of 2-acetamido-2-deoxy-β-D-glucopyranosylpolyethylene glycol-modified IFN-αA (i) Following the procedure of Reference Example 2, 53 mg of the aldehyde (mean molecular weight 1,300) obtained in Example 2-(iii) and 14 mg of sodium cyanoborohydride were reacted with IFN-α and the reaction mixture was treated in the same manner as in Reference Example 2 to give 42.5 ml of a main protein fraction. protein content of this fraction was 86 μg/ml. Amino acid analysis indicated that the 4.6 of 11 Lys residues in IFN-α had been modified. The activity determined by enzyme immunoassay was $0.70 \times 10^7$ international units per milligram.

(ii) Following the procedure of Reference Example 2, 107 mg of the aldehyde (mean molecular weight 1,300) obtained in Example 2-(iii) and 28 mg of sodium cyanoborohydride were reacted with IFN-α and the reaction mixture was treated in the same manner as in Reference Example 2 to give 24.5 ml of a main protein fraction. The protein content of this fraction was 138 μg/ml. Amino acid analysis showed that 6.9 of 11 Lys residues in IFN-α had been modified. The activity as determined by enzyme immunoassay was 0.83 × 10⁶ international units per milligram.

(iii) Unmodified IFN-α, the polyethylene glycol-modified IFN-α obtained in Reference Example 1-(ii) and the two species of 2-actamido-2-deoxy-β-D-glucopyranosylpolyethylene glycol-modified IFN-α as obtained as mentioned above in (i) and (ii) were subjected to affinity chromatography using WGA-Agarose (Hohnen Seiyu), an agarose gel coupled with wheat germ lectin, which is able to recognize and bind specifically to a nonreducing β-N-acetylglucosamine endgroup. Unmodified IFN-α and the polyethylene glycol-modified IFN-α were not adsorbed on the column but passed through it. It was confirmed that the 2-acetamido-2-deoxy-β-D-glucopyranosylpolyethylene glycol-modified IFN-α species were adsorbed on WGA-Agarose and that the degree of adsorption increased with the increase in the extent of modification.

The results obtained are shown in FIG. 2. In FIG. 2, charts (a), (b), (c) and (d) show the elution patterns of unmodified IFN-α, the polyethylene glycolmodified IFN-α and the two 2-acetamido-2-deoxy-β-D-glucopyranosylpolyethylene glycol-modified IFN-α species, respectively, obtained by monitoring the absorbance at 280 nm. In each chart, arrow 1 indicates the time when each sample solution dissolved in 25 mM ammonium acetate buffer (pH 5.0) containing 0.15 M sodium chloride was charged, arrow 2 the time when the eluent was changed from 25 mM ammonium acetate buffer (pH 5.0) containing 0.15 M sodium chloride to 25 mM ammonium acetate buffer (pH 5.0) containing 2-propenyl-2-acetamido-2-deoxy-β-D-glucopyranoside in a concentration of 10 mM and 0.15 M sodium chloride, and arrow 3 the time when the eluent was changed to the initial 25 mM ammonium acetate buffer (pH 5.0) containing 0.15 M sodium chloride.

What is claimed is:

1. A compound of the formula (I):

R—O—$(CH_2CH_2O)_m(CH_2)_n$—Z wherein R is a monosaccharide glycosyl group or an oligosaccharide glycosyl group, m is a positive integer up to about 200, n is an integer from 1 to 3 and Z is —CHO or —COOH.

2. The compound according to claim 1, wherein R is selected from the group consisting of arabinopyranopyranosyl, xylopyranosyl, lyxopyranosyl, ribofuranosyl, glucopyranosyl, galactopyranosyl, mannopyranosyl, fucopyranosyl, 2-amino-2-deoxyglupyranosyl, 2-amino-2-deoxygalactopyranosly, 2-acetamido-2-deoxyglucopyranosyl, 2-acetamido-2-deoxygalactopyranosyl, N-acetylneuraminyl, lactosyl, xylobiosyl, maltosyl, cellobiosyl, chitobiosyl, vicianosyl, sucrosyl, lactulosyl, rutinosyl, raffinosyl, umbelliferosyl, sialyllactosyl, 6'-galactolactosyl, difucosyllactosyl, lacto-N-tetraosyl and lacto-N-neotetraosyl.

3. The compound according to claim 1, wherein R is selected from the group consisting of glucopyranosyl, galactopyranosyl and 2-acetamido-2-deoxyglucopyranosyl.

4. The compound according to claim 1, wherein m is about 5 to 100.

* * * * *